US009119901B2

(12) United States Patent
Trieu et al.

(10) Patent No.: US 9,119,901 B2
(45) Date of Patent: Sep. 1, 2015

(54) SURFACE TREATMENTS FOR PROMOTING SELECTIVE TISSUE ATTACHMENT TO MEDICAL IMPANTS

(75) Inventors: Hai H. Trieu, Cordova, TN (US); Fred Molz, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2247 days.

(21) Appl. No.: 11/116,378

(22) Filed: Apr. 28, 2005

(65) Prior Publication Data

US 2006/0247793 A1 Nov. 2, 2006

(51) Int. Cl.
| | |
|---|---|
| A61F 2/28 | (2006.01) |
| A61L 27/50 | (2006.01) |
| A61F 2/30 | (2006.01) |
| A61L 27/54 | (2006.01) |
| A61L 31/16 | (2006.01) |

(52) U.S. Cl.
CPC ............ *A61L 27/50* (2013.01); *A61F 2/30767* (2013.01); *A61L 27/54* (2013.01); *A61L 31/16* (2013.01); *A61F 2002/30028* (2013.01); *A61F 2002/3093* (2013.01); *A61F 2002/30932* (2013.01); *A61F 2250/0051* (2013.01); *A61L 2300/414* (2013.01); *A61L 2400/18* (2013.01)

(58) Field of Classification Search
CPC ............................ A61L 27/50; A61F 2/30767
USPC ......... 623/23.72, 23.74, 23.76; 606/151, 155; 600/37
See application file for complete search history.

(56) References Cited

U.S. PATENT DOCUMENTS

| | | | |
|---|---|---|---|
| 4,346,108 A | 8/1982 | Singer | |
| 4,603,695 A | 8/1986 | Ikada et al. | |
| 4,672,031 A | 6/1987 | Prockop | |
| 4,704,131 A | 11/1987 | Noishiki et al. | |
| 4,749,585 A | 6/1988 | Greco et al. | |
| 4,781,591 A * | 11/1988 | Allen ........................... 433/174 |
| 4,840,626 A | 6/1989 | Linsky et al. | |
| 4,938,763 A | 7/1990 | Dunn et al. | |
| 5,007,916 A | 4/1991 | Linsky et al. | |
| 5,073,373 A | 12/1991 | O'Leary et al. | |
| 5,134,229 A | 7/1992 | Saferstein et al. | |
| 5,156,839 A | 10/1992 | Pennell et al. | |
| 5,190,759 A | 3/1993 | Lindblad et al. | |
| 5,219,895 A | 6/1993 | Kelman et al. | |
| 5,257,632 A | 11/1993 | Turkel et al. | |
| 5,278,201 A | 1/1994 | Dunn et al. | |
| 5,278,202 A | 1/1994 | Dunn et al. | |
| 5,326,354 A | 7/1994 | Kwarteng | |
| 5,358,973 A | 10/1994 | Lindblad et al. | |
| 5,397,796 A | 3/1995 | Zoeller et al. | |
| 5,412,068 A | 5/1995 | Tang et al. | |
| 5,502,042 A | 3/1996 | Gruskin et al. | |
| 5,505,952 A | 4/1996 | Jiang et al. | |
| 5,508,036 A | 4/1996 | Bakker et al. | |
| 5,509,899 A | 4/1996 | Fan et al. | |
| 5,534,524 A | 7/1996 | Bonewald et al. | |
| 5,554,594 A | 9/1996 | Zoeller et al. | |
| 5,583,114 A | 12/1996 | Barrows et al. | |
| 5,612,321 A | 3/1997 | Nguyen | |
| 5,628,781 A * | 5/1997 | Williams et al. ............. 623/1.39 |
| 5,652,224 A | 7/1997 | Wilson et al. | |
| 5,658,935 A | 8/1997 | Klingler et al. | |
| 5,711,958 A | 1/1998 | Cohn et al. | |
| 5,756,145 A | 5/1998 | Darouiche | |
| 5,795,584 A | 8/1998 | Totakura et al. | |
| 5,807,833 A | 9/1998 | Dizerega | |
| 5,846,530 A | 12/1998 | Soon-Shiong et al. | |
| 5,874,537 A | 2/1999 | Kelman et al. | |
| 5,931,165 A | 8/1999 | Reich et al. | |
| 5,947,893 A | 9/1999 | Agrawal et al. | |
| 5,962,006 A | 10/1999 | Southard et al. | |
| 5,993,890 A | 11/1999 | Marchant et al. | |
| 5,994,133 A * | 11/1999 | Meijs et al. ................... 435/395 |
| 6,007,833 A | 12/1999 | Chudzik et al. | |
| 6,030,958 A | 2/2000 | Burns et al. | |
| 6,031,069 A | 2/2000 | Oberhoffner et al. | |
| 6,031,148 A | 2/2000 | Hayes et al. | |
| 6,034,088 A | 3/2000 | Reeve et al. | |
| 6,034,140 A | 3/2000 | Schwartz et al. | |
| 6,037,331 A | 3/2000 | Shalaby et al. | |
| 6,063,061 A | 5/2000 | Wallace et al. | |
| 6,074,663 A | 6/2000 | Delmotte et al. | |

(Continued)

FOREIGN PATENT DOCUMENTS

| | | |
|---|---|---|
| EP | 0401384 A1 | 12/1990 |
| EP | 1084720 | 3/2001 |
| EP | 1 340 476 A1 | 9/2003 |
| WO | WO 90/11092 | 10/1990 |
| WO | WO-9705238 | 2/1997 |
| WO | 9718904 A1 | 5/1997 |
| WO | 9749434 A3 | 12/1997 |
| WO | 9850050 A1 | 11/1998 |
| WO | 9853800 A1 | 12/1998 |
| WO | 9958186 A1 | 11/1999 |

(Continued)

OTHER PUBLICATIONS

International Search Report, mailed Jun. 14, 2007, 3 pages.

*Primary Examiner* — Bruce E Snow
*Assistant Examiner* — Melissa Hoban
(74) *Attorney, Agent, or Firm* — Sorell Lenna & Schmidt LLP

(57) ABSTRACT

Embodiments include a method for promoting selective tissue attachment to medical implants. By treating implant surfaces where tissue attachment is desired with tissue attachment promoting treatments, and treating implant surfaces where tissue attachment is not desired with tissue attachment inhibiting treatments, selective tissue attachment to medical implants may be achieved. Also, embodiments include an implant with at least one tissue contacting surface and at least one secondary surface where tissue attachment is not desired, and appropriate tissue attachment promoting or inhibiting treatments on the surfaces.

20 Claims, No Drawings

(56) References Cited

U.S. PATENT DOCUMENTS

| | | | |
|---|---|---|---|
| 6,093,388 A | 7/2000 | Ferguson | |
| 6,096,727 A | 8/2000 | Kuo et al. | |
| 6,113,636 A | 9/2000 | Ogle | |
| 6,131,580 A | 10/2000 | Ratner et al. | |
| 6,133,325 A | 10/2000 | Schwartz et al. | |
| 6,136,333 A | 10/2000 | Cohn et al. | |
| 6,139,585 A | 10/2000 | Li | |
| 6,150,581 A | 11/2000 | Jiang et al. | |
| 6,153,252 A | 11/2000 | Hossainy et al. | |
| 6,156,345 A | 12/2000 | Chudzik et al. | |
| 6,162,487 A | 12/2000 | Darouiche | |
| 6,174,855 B1 | 1/2001 | Hansson | |
| 6,217,894 B1 | 4/2001 | Sawhney et al. | |
| 6,231,892 B1* | 5/2001 | Hubbell et al. | 424/491 |
| 6,235,796 B1 | 5/2001 | Niazi | |
| 6,261,586 B1 | 7/2001 | McKay | |
| 6,280,745 B1 | 8/2001 | Flore et al. | |
| 6,290,729 B1* | 9/2001 | Slepian et al. | 623/23.72 |
| 6,294,041 B1* | 9/2001 | Boyce et al. | 156/275.5 |
| 6,302,909 B1 | 10/2001 | Ogle et al. | |
| 6,306,922 B1 | 10/2001 | Hubbell et al. | |
| 6,312,725 B1 | 11/2001 | Wallace et al. | |
| 6,313,119 B1 | 11/2001 | Peyman et al. | |
| 6,317,275 B1 | 11/2001 | Yoneyama | |
| 6,328,765 B1 | 12/2001 | Hardwick et al. | |
| 6,333,029 B1 | 12/2001 | Vyakarnam et al. | |
| 6,350,527 B1 | 2/2002 | Hubbell et al. | |
| 6,352,710 B2 | 3/2002 | Sawhney et al. | |
| 6,372,256 B2 | 4/2002 | Jamiolkowski et al. | |
| 6,391,939 B2 | 5/2002 | Tayot et al. | |
| 6,399,264 B1 | 6/2002 | Ogata et al. | |
| 6,410,044 B1 | 6/2002 | Chudzik et al. | |
| 6,410,645 B1 | 6/2002 | Pathak et al. | |
| 6,413,549 B2 | 7/2002 | Green et al. | |
| 6,436,425 B1 | 8/2002 | Henry et al. | |
| 6,440,427 B1 | 8/2002 | Wadstrom | |
| 6,455,541 B1 | 9/2002 | Bonewald et al. | |
| 6,458,889 B1 | 10/2002 | Trollsas et al. | |
| 6,478,822 B1* | 11/2002 | Leroux et al. | 623/17.14 |
| 6,486,140 B2 | 11/2002 | Hansson et al. | |
| 6,492,356 B1 | 12/2002 | Peyman et al. | |
| 6,492,494 B1 | 12/2002 | Cederholm-Williams | |
| 6,517,888 B1 | 2/2003 | Weber | |
| 6,521,223 B1 | 2/2003 | Calias et al. | |
| 6,527,938 B2 | 3/2003 | Bales et al. | |
| 6,531,147 B2 | 3/2003 | Sawhney et al. | |
| 6,534,591 B2 | 3/2003 | Rhee et al. | |
| 6,537,979 B1 | 3/2003 | Kuo et al. | |
| 6,548,081 B2 | 4/2003 | Sadozai et al. | |
| 6,551,610 B2 | 4/2003 | Shalaby et al. | |
| 6,552,170 B1 | 4/2003 | Thompson et al. | |
| 6,565,489 B2 | 5/2003 | Ho et al. | |
| 6,566,345 B2 | 5/2003 | Miller et al. | |
| 6,596,267 B1 | 7/2003 | Hubbell et al. | |
| 6,596,338 B2 | 7/2003 | Scott et al. | |
| 6,599,526 B2 | 7/2003 | Dimitrijevich | |
| 6,602,975 B2 | 8/2003 | Hubbell et al. | |
| 6,610,669 B1 | 8/2003 | Calias et al. | |
| 6,613,325 B1 | 9/2003 | Amery et al. | |
| 6,613,432 B2 | 9/2003 | Zamora et al. | |
| 6,630,167 B2 | 10/2003 | Zhang | |
| 6,656,345 B1 | 12/2003 | Chen et al. | |
| 6,673,361 B1 | 1/2004 | Ogura et al. | |
| 6,673,362 B2 | 1/2004 | Calhoun et al. | |
| 6,676,987 B2 | 1/2004 | Zhong et al. | |
| 6,685,956 B2 | 2/2004 | Chu et al. | |
| 6,689,374 B2 | 2/2004 | Chu et al. | |
| 6,689,903 B2 | 2/2004 | O'Meadhra et al. | |
| 6,693,089 B1 | 2/2004 | Li et al. | |
| 6,696,499 B1 | 2/2004 | Cohn et al. | |
| 6,703,041 B2 | 3/2004 | Burns et al. | |
| 6,704,604 B2* | 3/2004 | Soukup et al. | 607/116 |
| 6,706,780 B2 | 3/2004 | Goldberg et al. | |
| 6,719,960 B1 | 4/2004 | Hills et al. | |
| 6,720,469 B1* | 4/2004 | Curtis et al. | 602/41 |
| 6,723,709 B1 | 4/2004 | Pressato et al. | |
| 6,726,718 B1* | 4/2004 | Carlyle et al. | 623/2.42 |
| 6,736,823 B2* | 5/2004 | Darois et al. | 606/151 |
| 6,736,849 B2 | 5/2004 | Li et al. | |
| 6,743,463 B2 | 6/2004 | Weber et al. | |
| 6,743,521 B2 | 6/2004 | Hubbell et al. | |
| 6,746,485 B1 | 6/2004 | Zucherman et al. | |
| 6,746,685 B2* | 6/2004 | Williams | 424/424 |
| 6,749,639 B2 | 6/2004 | Lewallen | |
| 6,749,685 B2* | 6/2004 | Coleman | 117/84 |
| 6,764,709 B2 | 7/2004 | Flanagan | |
| 6,780,427 B2 | 8/2004 | Baker et al. | |
| 6,861,088 B2 | 3/2005 | Weber et al. | |
| 7,144,588 B2* | 12/2006 | Oray et al. | 424/551 |
| 2002/0001584 A1 | 1/2002 | Metzner et al. | |
| 2002/0016635 A1* | 2/2002 | Despres et al. | 623/23.5 |
| 2002/0049495 A1* | 4/2002 | Kutryk et al. | 623/1.47 |
| 2002/0147486 A1* | 10/2002 | Soukup et al. | 607/122 |
| 2002/0156529 A1 | 10/2002 | Li et al. | |
| 2002/0168406 A1 | 11/2002 | Goldenberg et al. | |
| 2002/0198601 A1 | 12/2002 | Bales et al. | |
| 2003/0065292 A1 | 4/2003 | Darouiche et al. | |
| 2003/0069354 A1 | 4/2003 | Oyasato et al. | |
| 2003/0073663 A1 | 4/2003 | Wiseman et al. | |
| 2003/0077381 A1 | 4/2003 | Scott et al. | |
| 2003/0094719 A1 | 5/2003 | Yang et al. | |
| 2003/0100739 A1 | 5/2003 | Tsai et al. | |
| 2003/0108659 A1 | 6/2003 | Bales et al. | |
| 2003/0124087 A1 | 7/2003 | Kim et al. | |
| 2003/0133928 A1 | 7/2003 | Metzner et al. | |
| 2003/0170378 A1 | 9/2003 | Wen et al. | |
| 2003/0171825 A1* | 9/2003 | Blunn et al. | 623/32 |
| 2003/0176927 A1* | 9/2003 | Steinemann et al. | 623/23.55 |
| 2003/0180251 A1 | 9/2003 | Friedrich et al. | |
| 2004/0001911 A1 | 1/2004 | Scott et al. | |
| 2004/0009917 A1 | 1/2004 | Redl et al. | |
| 2004/0024081 A1* | 2/2004 | Trieu et al. | 523/113 |
| 2004/0043016 A1 | 3/2004 | Redl | |
| 2004/0043052 A1 | 3/2004 | Hunter et al. | |
| 2004/0092433 A1 | 5/2004 | Wang et al. | |
| 2004/0115241 A1 | 6/2004 | Calhoun et al. | |
| 2004/0126420 A1 | 7/2004 | Dobbie | |
| 2004/0131754 A1 | 7/2004 | Zitelli et al. | |
| 2004/0141956 A1 | 7/2004 | Oray et al. | |
| 2004/0171545 A1 | 9/2004 | Chaikof et al. | |
| 2004/0185084 A1 | 9/2004 | Rhee et al. | |
| 2004/0249472 A1 | 12/2004 | Liu et al. | |
| 2005/0008620 A1* | 1/2005 | Shimp et al. | 424/93.7 |
| 2005/0033417 A1 | 2/2005 | Borges et al. | |
| 2005/0171604 A1* | 8/2005 | Michalow | 623/14.12 |

FOREIGN PATENT DOCUMENTS

| | | |
|---|---|---|
| WO | 0072856 A1 | 12/2000 |
| WO | 0217824 A2 | 3/2002 |
| WO | 0217853 A2 | 3/2002 |
| WO | 0244276 A2 | 6/2002 |
| WO | 03000344 A1 | 1/2003 |
| WO | 2004010854 A2 | 2/2004 |
| WO | 2004021983 2 A | 3/2004 |

\* cited by examiner

SURFACE TREATMENTS FOR PROMOTING SELECTIVE TISSUE ATTACHMENT TO MEDICAL IMPANTS

FIELD OF THE INVENTION

Embodiments of the invention relate to surface treatments for medical implants. More particularly, embodiments relate to treating portions of implants where tissue attachment is desired with tissue attachment promoting treatments, and treating portions of the implants where tissue attachment is not desired with tissue attachment inhibiting treatments.

BACKGROUND

Medical implants or prostheses function to replace or augment various structures and tissues in the body. Medical implants include, for example, intervertebral disc replacement devices, spinal fixation systems, facet arthroplasty devices, artificial hips, bone screws, bone plates and rods, prosthetic knee replacements, arterial stents, pacemakers, heart valves, artificial hearts, artificial sphincters, etc. The effectiveness of medical implants sometimes is highly dependent upon the implant's interactions with surrounding tissues. For example, in the case of bone implants, it may be desirable that tissue attachment from adjacent bony structures occur at the bone implant's surface in order to integrate the bone implant with the rest of the skeletal system. Therefore, various surface treatments for medical implants have been proposed in order to stimulate attachment of a wide variety of tissues.

The description herein of problems and disadvantages of known apparatus, methods, and devices is not intended to limit the invention to the exclusion of these known entities. Indeed, embodiments of the invention may include one or more of the known apparatus, methods, and devices without suffering from the disadvantages and problems noted herein.

SUMMARY OF THE INVENTION

There is a need for a method of more fully regulating the interactions between medical implants and surrounding tissues. There also is a need for a method that stimulates advantageous interactions of medical implants and surrounding tissues, and that discourages disadvantageous interactions of medical implants and surrounding tissues. Additionally, there is a need for a method to guide tissue attachment to medical implants. Medical implants with surface treatments to selectively promote tissue attachment also are needed. Embodiments of the invention solve some or all of these needs, as well as additional needs.

Therefore, in accordance with an embodiment of the present invention, there is provided a method for promoting selective tissue attachment to medical implants. Surfaces of the medical implant where tissue attachment is desired may be treated with a tissue attachment promoting treatment. Surfaces of the medical implant where tissue attachment is not desirable may be treated with a tissue attachment inhibiting treatment.

In accordance with another embodiment of the present invention, there is provided an implant and a system including the implant, whereby the implant comprises at least one tissue contacting surface, and at least one secondary surface where tissue attachment is not desirable. The at least one tissue contacting surface may be treated with a tissue attachment promoting treatment. Also, the at least one secondary surface may be treated with a tissue attachment inhibiting treatment. The system further can comprise other components implanted with the implant.

These and other features and advantages of the present invention will be apparent from the description of exemplary embodiments of the invention provide herein.

DETAILED DESCRIPTION OF THE EMBODIMENTS

The following description is intended to convey a thorough understanding of exemplary embodiments of the invention by providing a number of specific embodiments and details involving surface treatments for promoting selective tissue attachment to medical implants. It is understood, however, that the present invention is not limited to these specific embodiments and details, which are exemplary only. It is further understood that one possessing ordinary skill in the art, in light of known systems and methods, would appreciate the use of the invention for its intended purposes and benefits in any number of alternative embodiments.

It is a feature of an embodiment of the present invention to provide a method for promoting selective tissue attachment to medical implants. Surfaces of the medical implant where tissue attachment is desired may be treated with a tissue attachment promoting treatment. Surfaces of the medical implant where tissue attachment is not desirable may be treated with a tissue attachment inhibiting treatment.

Medical implants according to the embodiments are useful in enhancing the attachment of endogenous (natural) tissues to the medical implants. The increased rate of endogenous tissue attachment may result in an increased rate and degree of implant adhesion to the endogenous tissues. The increased rate of endogenous tissue attachment also may decrease the amount of time necessary for the medical implant to achieve stability in the patient, thereby decreasing the recovery time of the implant patient. The increased degree of endogenous tissue attachment additionally may enhance the stability of the medical implant by helping to minimize the ability of bodily fluids or wear debris to impact the interface of the medical implant and endogenous tissues, which could play a role in failure of the medical implant.

Additionally, medical implants according to the embodiments are useful in enhancing the selectivity of tissue attachment to surfaces of medical implants. While tissue attachment may be advantageous on some surfaces of the implant for the reasons described herein, on other surfaces of the implant tissue attachment may be undesirable. For example, it may be disadvantageous for tissue attachment to occur on surfaces of the implant that articulate against one another because the presence of tissues on articulating surface may impede proper articulation. One skilled in the art will recognize still other implant surfaces where tissue attachment is to be avoided. By selectively treating implant surfaces where tissue attachment is not desired with tissue attachment inhibiting treatments, tissue attachment can be prevented or at least substantially discouraged at these surfaces.

Additionally, it may be desirable to promote the attachment of a specific type or types of tissues to surfaces of a medical implant, while inhibiting the attachment of another type or types of tissues to surfaces of a medical implant. Therefore, in a preferred embodiment, various tissue attachment promoting treatments and inhibiting treatments may be applied to the surfaces of a medical implant dependent upon the type of tissues that are to be, respectively, promoted or inhibited from attaching to the surface of the implants. For example, an implant may have one surface with a treatment for promoting the attachment of bone, another surface with a treatment for promoting the attachment of muscle, and another surface with a tissue attachment inhibiting treatment for preventing attachment of any type of tissue. One skilled in the art therefore will recognize that the inhibiting and promoting treatments may vary dependant upon the type of living tissue that is to be, respectively, inhibited or promoted.

Also, surface areas where one type of tissue attachment is to be promoted or inhibited and surface areas where another type of tissue attachment is to be promoted or inhibited may overlap. One skilled in the art therefore also will recognize that the surfaces to which the inhibiting and promoting treatments are to be applied may overlap. Embodiments allow overlapping surface areas of the implant to be selectively treated with tissue promoting and inhibiting treatments, according to the type of tissue that is to be promoted or inhibited in attaching to the implant.

In a preferred embodiment of the invention, only surfaces of the implant where tissue attachment is desired are treated with a tissue attachment promoting treatment. In another preferred embodiment of the invention, only surfaces of the implant where tissue attachment is not desired are treated with a tissue attachment inhibiting treatment. In another preferred embodiment of the invention, all surfaces of the implant are treated with a tissue attachment inhibiting treatment, except for surfaces where tissue attachment is desired, which may be treated with a tissue attachment promoting treatment. In an additional embodiment, all surfaces are treated with a tissue attachment inhibitory treatment, and then those surfaces where tissue attachment is desired are additionally treated with a tissue attachment promoting treatment, or vice versa, as the case may be. Accordingly, preferred embodiments provide medical implants with selectively promoted and inhibited tissue attachment, which may lead to a better clinical outcome following implantation.

Any applicable tissue attachment promoting treatment may be used in accordance with embodiments the present invention. Embodiments are not restricted to a certain class or type of tissue attachment promoting treatments, but rather encompasses all such known and yet-to-be discovered treatments. Tissue attachment promoting treatments are those that promote tissue attachment at or near the sites of treatment and provide greater tissue attachment, when compared to an identical surface that has not been treated. Tissue attachment promoting treatments may promote the in-growth or on-growth into the implant of, for example, connective tissue, vascular tissue, nerve tissues, scar tissue, ligaments, tendons, skin, endogenous bone (cancellous or cortical), muscle, and aid in preventing the resorption of bone tissue. Preferred tissue attachment promoting treatments include tissue attachment components (i.e., biologically active agents for promoting tissue in-growth and on-growth). Preferred agents include osteoconductive and osteoinductive agents for promoting the attachment of endogenous bone. The tissue attachment promoting components may be mixed into formulations comprising, for example, the active agents and saline, water, or other solvents or carriers. Described herein are some exemplary tissue attachment promoting formulations for use in accordance with the embodiments.

Tissue attachment promoting formulations useful for promoting the attachment of endogenous tissues may comprise bone morphogenetic factors. Bone morphogenetic factors are growth factors whose activity is specific to bone tissue including, but not limited to, demineralized bone matrix (DBM), bone protein (BP), bone morphogenetic protein (BMP), and mixtures and combinations thereof. Methods for producing DBM are well known in the art, and DBM may be obtained following the teachings of O'Leary et al. (U.S. Pat. No. 5,073,373) or by obtaining commercially available DBM formulations such as, for example, AlloGro® (commercially available from AlloSource, Centennial, Colo.). Additionally, formulations for promoting the attachment of endogenous bone may comprise bone marrow aspirate, bone marrow concentrate, and mixtures and combinations thereof. Methods of obtaining bone marrow aspirates as well as devices facilitating extraction of bone marrow aspirate are well known in the art and are described, for example, by Turkel et al. in U.S. Pat. No. 5,257,632.

Tissue attachment promoting formulations optionally may further comprise antibiotics and antiretroviral drugs. As discussed by Vehmeyer et al., the possibility exists that bacterial contamination can occur, for example, due to the introduction of contaminated allograft tissue from living donors. Vehmeyer, S B, et al., Acta Orthop Scand., 73(2):165-169 (2002). Antibiotics and antiretroviral drugs may be administered to prevent infection by pathogens that are introduced to the patient during implant surgery. Also, administration of antibiotics and antiretroviral drugs may be useful to account for nosocomial infections or other factors specific to the location where the implant surgery is conducted. Antibiotics and antiretroviral drugs useful in the tissue attachment promoting formulations include, but are not limited to, aminoglycosides such as tobramycin, amoxicillin, ampicillin, azactam, bacitracin, beta-lactamases, beta-lactam (glycopeptide), biomycin, clindamycin, chloramphenicol, chloromycetin, cefazolin, cephalosporins, ciprofloxacin, erythromycin, fluoroquinolones, gentamicin, macrolides, metronidazole, neomycin, penicillins, polymycin B, quinolones, rapamycin, rifampin, streptomycin, sulfonamide, tetracyclines, trimethoprim, trimethoprim-sulfamethoxazole, vancomycin, and mixtures and combinations thereof.

The tissue attachment promoting formulations optionally may further comprise immunosuppressive agents, particularly in circumstances where an implant comprising an allograft composition is delivered to the patient. Suitable immunosuppressive agents that may be administered in combination with the tissue attachment promoting formulations include, but are not limited to, steroids, cyclosporine, cyclosporine analogs, cyclophosphamide, methylprednisone, prednisone, azathioprine, FK-506, 15-deoxyspergualin, and other immunosuppressive agents that act by suppressing the function of responding T cells. Other immunosuppressive agents that may be administered in combination with the tissue attachment promoting formulations include, but are not limited to, prednisolone, methotrexate, thalidomide, methoxsalen, rapamycin, leflunomide, mizoribine (bredininTM), brequinar, deoxyspergualin, and azaspirane (SKF 105685), Orthoclone OKTTM 3 (muromonab-CD3). Sandimmune™, Neoral™, Sangdya™ (cyclosporine), Prograf™ (FK506, tacrolimus), Cellcep™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrexate), Oxsoralen-Ultra™ (methoxsalen) and Rapamuen™ (sirolimus).

The tissue attachment promoting formulations optionally may comprise substances that enhance isotonicity and chemical stability. Such materials are non-toxic to patients at the dosages and concentrations employed, and include buffers such as phosphate, citrate, succinate, acetic acid, and other organic acids or their salts; antioxidants such as ascorbic acid; low molecular weight (less than about ten residues) polypeptides such as polyarginine and tripeptides; proteins such as serumalbumin, gelatin, and immunoglobulins; amino acids such as glycine, glutamic acid, aspartic acid, and arginine; monosaccharides, disaccharides, and other carbohydrates including cellulose and its derivatives, glucose, mannose, and dextrans; chelating agents such as EDTA; sugaralcohols such as mannitol and sorbitol; counterions such as sodium; non-ionicsurfactants such as polysorbates, poloxamers, and polyethylene glycol PEG; and mixtures and combinations thereof.

The tissue attachment promoting formulations may comprise osteoinductive and osteoconductive agents. Such agents include, but are not limited to members of the families of Bone Morphogenetic Proteins (BMPs), Osteoprotegerin or any of the other osteoclastogenesis inhibitors, Connective Tissue Growth Factors (CTGFs), Vascular Endothelial Growth Factors (VEGFs), Transforming Growth Factor-betas (TGF-bs), Growth Differentiation Factors (GDFs), Cartilage Derived Morphogenic Proteins (CDMPs), and Lim Mineralization Proteins (LMPs).

BMPs are a class of proteins thought to have osteoinductive or growth-promoting activities on endogenous bone tissue, or function as pro-collagen precursors. Known members of the BMP family that may be utilized as osteoinductive agents in tissue attachment formulations include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18 polynucleotides and polypeptides, as well as mature polypeptides and polynucleotides encoding the same. The BMPs may be included in the implants as full length BMPs or fragments thereof, or combinations or mixtures thereof, or as polypeptides or polynucleotides encoding the polypeptide fragments of all of the recited BMPs.

Osteoclastogenesis inhibitors inhibit bone resorption by osteoclasts of the bone tissue surrounding the site of implantation. Osteoclast and Osteoclastogenesis inhibitors include, but are not limited to, Osteoprotegerin polynucleotides and polypeptides, as well as mature Osteoprotegerin polypeptides and polynucleotides encoding the same. The Osteoprotegerin protein specifically binds to its ligand, osteoprotegerin ligand (TNFSF11/OPGL), both of which are key extracellular regulators of osteoclast development. Osteoclastogenesis inhibitors further include, but are not limited to, chemical compounds such as bisphosphonate, 5-lipoxygenase inhibitors such as those described in U.S. Pat. Nos. 5,534,524 and 6,455,541 (herein incorporated by reference), heterocyclic compounds such as those described in U.S. Pat. No. 5,658,935 (herein incorporated by reference), 2,4-dioxoimidazolidine and imidazolidine derivative compounds such as those described in U.S. Pat. Nos. 5,397,796 and 5,554,594 (herein incorporated by reference), sulfonamide derivatives such as those described in U.S. Pat. No. 6,313,119 (herein incorporated by reference), and acylguanidine compounds such as those described in U.S. Pat. No. 6,492,356 (herein incorporated by reference).

CTGFs are a class of proteins thought to have growth-promoting activities on connective tissues. Known members of the CTGF family include, but are not limited to, CTGF-1, CTGF-2, and CTGF-4, any of which may be incorporated into the tissue attachment formulations of the embodiments, in addition to polypeptides and polynucleotides encoding the same.

VEGFs are a class of proteins thought to have growth-promoting activities on vascular tissues. Known members of the VEGF family include, but are not limited to, VEGF-A, VEGF-B, VEGF-C, VEGF-D and VEGF-E, any of which may be incorporated into the tissue attachment formulations of the embodiments, in addition to polypeptides and polynucleotides encoding the same.

TGF-bs are a class of proteins thought to have growth-promoting activities on a range of tissues, including connective tissues. Known members of the TGF-b family include, but are not limited to, TGF-b-1, TGF-b-2, and TGF-b-3, any of which may be incorporated into the tissue attachment formulations of the embodiments, in addition to polypeptides and polynucleotides encoding the same.

Known GDFs include, but are not limited to, GDF-1, GDF-2, GDF-3, GDF-7, GDF-10, GDF-11, and GDF-15. GDF-1 polynucleotides and polypeptides correspond to GenBank Accession Numbers M62302, AAA58501, and AAB94786; GDF-2 polynucleotides and polypeptides correspond to GenBank Accession Numbers BC069643, BC074921, Q9UK05, AAH69643, and AAH74921; GDF-3 polynucleotides and polypeptides correspond to GenBank Accession Numbers AF263538, BC030959, AAF91389, AAQ89234, and Q9NR23; GDF-7 polynucleotides and polypeptides correspond to GenBank Accession Numbers AB158468, AF522369, AAP97720, and Q7Z4P5; GDF-10 polynucleotides and polypeptides correspond to GenBank Accession Numbers BC028237 and AAH28237; GDF-11 polynucleotides and polypeptides correspond to GenBank Accession Numbers AF100907, NP_005802 and 095390; and GDF-15 polynucleotides and polypeptides correspond to GenBank Accession Numbers BC008962, BC000529, AAH00529, and NP_004855.

Known CDMPs and LMPs include, but are not limited to, CDMP-1, CDMP-2, LMP-1, LMP-2, and LMP-3. CDMP-1 polynucleotides and polypeptides correspond to GenBank Accession Numbers NM_000557, U13660, NP_000548 and P43026; CDMP-2 polypeptides correspond to GenBank Accession Numbers and P55106; LMP-1 polynucleotides and polypeptides correspond to GenBank Accession Numbers AF345904 and AAK30567; LMP-2 polynucleotides and polypeptides correspond to GenBank Accession Numbers AF345905 and AAK30568; and LMP-3 polynucleotides and polypeptides correspond to GenBank Accession Numbers AF345906 and AAK30569.

Other osteoinductive and osteoconductive factors, agents, and compounds such as hydroxyapatite (HA), tricalcium phosphate (TCP), collagen, fibronectin (FN), osteonectin (ON), endothelial cell growth factor (ECGF), cementum attachment extracts (CAE), ketanserin, human growth hormone (HGH), animal growth hormones, epidermal growth factor (EGF), interleukin-1 (IL-1), human alpha thrombin, insulin-like growth factor (IGF-1), platelet derived growth factors (PDGF), and fibroblast growth factors (FGF, bFGF, etc.) also may be included in the tissue attachment promoting formulations.

Some of the tissue attachment compounds described herein may be polypeptide compositions, which may be delivered by gene therapy vectors harboring the polynucleotides encoding the polypeptide of interest. The vector may be, for example, a phage, plasmid, viral, or retroviral vector. The gene therapy vectors may be included only in portions of the implant where tissue attachment is desired. Gene therapy methods require a polynucleotide which codes for the desired polypeptide and any other genetic elements necessary for the expression of the polypeptide by the target tissue. Such gene therapy and delivery techniques are known in the art. See, for example, International Publication No. WO 90/11092, which is herein incorporated by reference. Gene therapy vectors further comprise suitable adenoviral vectors including, but not limited to, those described in Kozarsky and Wilson, Curr. Opin. Genet. Devel., 3:499-503 (1993); Rosenfeld et al., Cell, 68:143-155 (1992); Engelhardt et al., Human Genet. Ther., 4:759-769 (1993); Yang et al., Nature Genet., 7:362-369 (1994); Wilson et al., Nature, 365:691-692 (1993); and U.S. Pat. No. 5,652, 224; all of which are herein incorporated by reference.

Suitable gene therapy vectors include gene therapy vectors that do not integrate into the host genome and gene therapy vectors that integrate into the host genome. A desired polynucleotide also may be delivered in plasmid formulations. Plasmid DNA or RNA formulations refer to polynucleotide sequences encoding osteoinductive polypeptides that are free from any delivery vehicle that acts to assist, promote, or facilitate entry into the cell, including viral sequences, viral particles, liposome formulations, lipofectin or precipitating agents and the like.

Tissue attachment promoting agent polypeptides also may be available as heterodimers or homodimers, as well as multimers or combinations thereof. Recombinantly expressed proteins may be in native forms, truncated analogs, muteins, fusion proteins (e.g., fusion proteins with the FC portion of human IgG), and other constructed forms capable of inducing bone, cartilage, or other types of tissue formation as demonstrated by in vitro and ex vivo bioassays and in vivo implantation in mammals, including humans. Examples of preferred fusion proteins include, but are not limited to, ligand fusions between mature osteoinductive polypeptides and the FC portion of human Immunoglobulin G (IgG). Methods of making fusion proteins and constructs encoding the same are well known in the art.

Polypeptide compositions of the tissue attachment promoting formulations include, but are not limited to, full length proteins, fragments, and variants thereof. In a preferred embodiment, polypeptide fragments of the tissue attachment promoting formulations are propeptide forms of the isolated full length polypeptides. In a particularly preferred embodiment, polypeptide fragments of the tissue attachment promoting formulations are mature forms of the isolated full length polypeptides. Also preferred are the polynucleotides encoding the propeptide and mature polypeptides of the tissue attachment promoting agents. Preferred embodiments of variant tissue attachment promoting agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). Embodiments further contemplate the use of polynucleotides and polypeptides having at least 95% homology, more preferably 97%, and even more preferably 99% homology to the isolated tissue attachment promoting agent polynucleotides and polypeptides provided herein.

Other compounds that may be included in the tissue attachment promoting formulations include platelet derived growth factor (PDGF); insulin-related growth factor-I (IGF-I); insulin-related growth factor-II (IGF-II); fibroblast growth factor (FGF); beta-2-microglobulin (BDGF II); biocidal/biostatic sugars such as dextran and glucose; peptides; nucleic acid and amino acid sequences such as leptin antagonists, leptin receptor antagonists, and antisense leptin nucleic acids; vitamins; inorganic elements; co-factors for protein synthesis; hormones; endocrine tissue or tissue fragments; synthesizers; enzymes such as collagenase, peptidases, and oxidases; polymer cell scaffolds with parenchymal cells; angiogenic agents; antigenic agents; cytoskeletal agents; cartilage fragments; living cells such as chondrocytes, bone marrow cells, mesenchymal stem cells, natural extracts, genetically engineered living cells, or otherwise modified living cells; autogenous tissues such as blood, serum, soft tissue, and bone marrow; bioadhesives; periodontal ligament chemotactic factor (PDLGF); somatotropin; antitumor agents and chemotherapeutics such as cis-platinum, ifosfamide, methotrexate, and doxorubicin hydrochloride; immuno-suppressants; permeation enhancers such as fatty acid esters including laureate, myristate, and stearate monoesters of polyethylene glycol; bisphosphonates such as alendronate, clodronate, etidronate, ibandronate, (3-amino-1-hydroxypropylidene)-1,1-bisphosphonate (APD), dichloromethylene bisphosphonate, aminobisphosphonatezolendronate, and pamidronate; pain killers and anti-inflammatories such as non-steroidal anti-inflammatory drugs (NSAID) like ketorolac tromethamine, lidocaine hydrochloride, bipivacaine hydrochloride, and ibuprofen; and salts such as strontium salt, fluoride salt, magnesium salt, and sodium salt.

Besides active tissue attachment promoting agents, the tissue attachment treatments may include physical transformation of the implant surface. For example, the creation of nano-scale surface features has been implicated as a promoter of biologic activity at the surface of medical implants. The creation of appropriately sized pores and surface roughening in general also has been implicated as a treatment for encouraging interaction between adjacent tissues and medical implants. Any applicable method can be used in order to effect a tissue attachment promoting physical transformation of the implant surfaces, including, but not limited to, machining, grinding, grit blasting, chemical etching, chemical vapor deposition, physical vapor deposition, electric discharge processes, laser etching, and the application of textured surfaces (e.g., textured cladding secured by welding, bonding, mechanical fixation, etc.).

Any applicable tissue attachment inhibiting treatment may be used on surfaces of the medical implants where tissue attachment is not desired, in accordance with the guidelines herein. Such inhibiting treatments may prevent or at least significantly discourage tissue attachment that might otherwise prevent proper in vivo functioning of the medical implant. Tissue attachment inhibitory treatments are those that inhibit tissue attachment at or near the sites of treatment and provide less tissue attachment (or no tissue attachment), when compared to an identical surface that was not so treated. For example, it may be desirable to treat surfaces of a bone implant that are not to be integrated with adjacent bony tissues with a treatment to prevent bone attachment to those surfaces. In another example, it may be desirable to treat surfaces of a fixation device such as a bone plate or rod that are external to the bony structures they are stabilizing with a treatment to prevent adjacent muscles, connective tissues, and vascular tissues from adhering to the fixation device. Preferably, the inhibiting treatment substantially reduces tissue in-growth and on-growth on the surface to which the treatment is applied.

One exemplary physical treatment to inhibit tissue attachment is to polish the desired surfaces of the implant to a high degree. It is believed that very smooth implant surfaces with relatively few microscopic or nano-scale defects inhibits interactions between the smooth surface and adjacent tissues. Polishing of the surfaces of the medical implants where tissue attachment is to be inhibited may proceed in any applicable manner. Polishing may be more preferred where the implant substrate is a metal or metal alloy as such surfaces lend themselves to polishing treatments. In an alterative, surfaces of the medical implant may be coated or cladded with metal, a metal alloy, or another substance that then can be polished or has been previously polished in order to inhibit tissue attachment. For example, the surfaces of the implant where tissue attachment is to be inhibited can be coated with polycrystalline diamond, which then can be polished to an extremely smooth surface, thereby inhibiting tissue interactions with the polycrystalline diamond coated surface. Another physical transformation to prevent or inhibit tissue attachment is to apply a bio-inert material to the surfaces where attachment is to be inhibited. Alternatively, a bio-resorbable material may be applied to the surfaces where attachment is to be inhibited. Any one or a combination of these physical treatments may be used to inhibit tissue attachment.

Another exemplary treatment to inhibit tissue attachment is to apply a tissue attachment inhibiting formulation in the same manner that a tissue attachment promoting formulation may be applied to other surfaces of the implant to promote tissue in-growth and on-growth. Inhibiting formulations may comprise various active agents or compounds that inhibit tissue in-growth or on-growth. One skilled in the art will appreciate the wide variety of inhibiting agents that can be used in accordance with the present invention. These inhibitory formulations can be applied to surfaces where tissue attachment is undesirable, as well as to surfaces where it may be desirable to delay tissue attachment, in which case an inhibitory formulation (or component or agent thereof) may be combined with a tissue attachment promoting treatment.

One exemplary class of inhibiting agents are chemotherapeutic agents. Chemotherapeutic agents can cause tissue growth to slow and therefore can be used to inhibit tissue attachment on selected implant surfaces. For example, chemotherapeutics such as 5-fluorouracil, Ara-C, anthracyclines, azathioprine, camptothecin, carmustine, cis-platinum, cyclophosphamide, dacarbazine, dactinomycin, doxorubicin hydrochloride, ifosfamide, interferon, irinotecan, methotrexate, novantrone, paclitaxel and derivatives and analogues thereof, procarbazine, pyrimethamine, tamoxifen, vinblastine, vincristine, and so forth are all contemplated by the embodiments for use in formulations to inhibit tissue attachment. Preferred chemotherapeutics are chemotherapeutics with a mode of action that is generally applicable to all cell lines. Another exemplary class of inhibiting agents are anti-adhesion agents or compounds, such as polyethylene glycol based anti-adhesion compounds.

The tissue attachment promoting and inhibiting treatments disclosed herein, including formulations of tissue attachment promoting and inhibiting compounds or agents, may be applied to any given medical implants. It should be understood that the tissue attachment promoting and inhibiting treatments are not limited to a specific type or category of medical implants, but are generally applicable to any medical implant where tissue attachment is to be encouraged on certain implant surfaces and discouraged on other implant surfaces. In a preferred embodiment, the tissue attachment promoting and inhibiting treatments are used with osteoimplants in order to direct the attachment of bony tissues to the implant.

Medical implants that are useful in embodiments of the current invention may be produced from a wide variety of materials, to which tissue attachment promoting and inhibiting treatments may be applied. For example, the medical implants may be fabricated from medical plastics such polyvinyl chlorides, polypropylenes, polystyrenes, acetal copolymers, polyphenyl sulfones, polycarbonates, acrylics, silicone polymers, polyetheretherketone (PEEK), polyurethanes, polyethylenes, polyethylene terphalate (PET), polymethylmethacrylate (PMMA), and mixtures and combinations thereof. Medical metals and metal alloys such as titanium, titanium alloys, tantalum, tantalum alloys, stainless steel alloys, cobalt-based alloys, cobalt-chromium alloys, cobalt-chromium-molybdenum alloys, niobium alloys, zirconium alloys, and shape memory alloys such as nitinol also may be used to fabricate the medical implants. Additionally, ceramics such as alumina, zirconia, hydroxyapatite, calcium phosphate, and PCDC may be used. Also, natural substrates such as allograft, xenograft, and autograft tissues may be used to fabricate the medical implants. Medical implants useful in the embodiments may also be composites of medical plastics, metals, alloys, ceramics, and natural tissues, particularly composites comprising carbon fibers or hydroxyapatite polymers.

Methods for producing medical implants are well known in the art and are largely dictated by the particular device that will be implanted. For example, general methods of manufacturing medical implants with porous or roughened surfaces are well known in the art, for example, through the use of sintering beads, machining of device surfaces, laser etching of surfaces, using nanotube technology to create roughened surfaces, casting roughened surfaces, and chemically etching roughened surfaces. In one embodiment, medical implants produced by these methods have an entirely porous composition. In another embodiment of the invention, medical implants produced by these methods have a porous surface layer. Porous medical implants may be produced by the deposition of surface layers that create porosity, or by using methods known in the art, for example by chemical or laser etching.

In a preferred embodiment, the medical implants have porous surfaces because the pores may function as reservoirs for formulations of tissue attachment promoting and inhibiting compounds and agents. In an embodiment of the invention, medical implants having a porous surface on at least a portion thereof are impregnated with tissue attachment promoting formulation only at surfaces of the implant where tissue attachment is desired. In another embodiment of the invention, medical implants having a porous surface on at least a portion thereof are impregnated with a tissue attachment inhibiting formulation only at surfaces of the implant where tissue attachment is not desired.

A method of producing an impregnated medical implant involves forming an implant having a porous surface on at least a portion thereof, and subsequently contacting only the porous surfaces of the implant where tissue attachment is desired with an applicable tissue attachment promoting formulation comprising a tissue attachment promoting compound or agent and contacting only the porous surfaces of the implant where tissue attachment is not desired with an applicable tissue attachment inhibiting formulation comprising a tissue attachment inhibiting compound or agent. The tissue attachment promoting and inhibiting formulations may be applied to the medical implant using any of a number of methods, such as by spraying, painting, soaking, dip-coating, spray-coating, solution coating, powder coating, or brushing the formulation onto the medical implant or immersing the medical implant in a solution comprising the tissue attachment formulation.

In an embodiment of the invention, the medical implant may be packaged without impregnated tissue attachment promoting and inhibiting formulations, such as for example where the medical implant comprises a porous substrate into which the tissue attachment promoting and inhibiting formulations are subsequently impregnated. In such a situation, tissue attachment promoting and inhibiting formulations generally may be placed into separate containers having sterile access ports such as a solution bag or vial having a stopper pierceable by a hypodermic injection needle. In a further embodiment, tissue attachment promoting and inhibiting formulations may be stored in separate containers, for example, sealed ampoules or vials, as aqueous solutions or as lyophilized formulations for reconstitution. As an example of a lyophilized formulation, 10-ml vials may be filled with 5 ml of a sterile-filtered 1% (w/v) aqueous tissue attachment promoting or inhibiting formulation, and the resulting mixture is lyophilized. The tissue attachment promoting and inhibiting formulations may be prepared by reconstituting the lyophilized agent prior to administration in an appropriate solution, and administering the formulation to the medical implant prior to, concurrent with, or after implantation into a patient.

As one of skill in the art will recognize, the concentrations of tissue attachment promoting and inhibiting agents may be variable based on the desired length or degree of action of the agents. Similarly, one of skill in the art will recognize that the tissue attachment promoting and inhibiting compounds and agents may be in immediate release formulations or sustained release formulations. Sustained release formulations are designed to provide tissue attachment promoting and inhibiting agents at relatively consistent concentrations in bioavailable form over extended periods of time.

In one embodiment of the invention, the tissue attachment promoting and inhibiting agents are associated with biodegradable sustained release polymers. The biodegradable sustained release polymers may be used to selectively coat surfaces of the implants dependent upon whether tissue attachment is or is not desired at an individual surface. Alternatively, the biodegradable sustained release polymers may be used as cladding that is selectively attached to surfaces of the implant surface dependent upon whether tissue attachment is or is not desired at an individual surface. Biodegradable sustained release polymers useful in sustained release formulations are well known in the art and include, but are not limited to, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, chitin, chitosan, poly(L-lactic acid), poly(lactide-co-glycolide), poly(hydroxybutyrate-co-valerate), and copolymers, terpolymers, or combinations or mixtures thereof. The release profile of the biodegradable polymer can further be modified by inclusion of biostable polymers that influence the biodegradation rate of the polymer composition, including, but not limited to, silicones, polyesters, vinyl homopolymers and copolymers, acrylate homopolymers and copolymers, polyethers, and cellulosics.

Another method to provide sustained release formulations that are useful for the delivery of tissue attachment promoting and inhibiting agents in vivo and permit the initial burst of active agent to be controlled more effectively than previously possible is to conjugate the active agent with a water-insoluble biocompatible polymer and dissolve the resultant polymer-active agent conjugate in a biocompatible solvent to form a liquid polymer system similar to that described in U.S. Pat. Nos. 4,938,763, 5,278,201 and 5,278,202. The water-insoluble biocompatible polymers may be those described in the above patents or related copolymers. In addition, the liquid polymer system also may include a water-insoluble biocompatible polymer which is not conjugated to the active agent. The water-insoluble biocompatible polymers then may be used to selectively coat surfaces of the implants dependent upon whether tissue attachment is or isn't desired at an individual surface.

Tissue attachment promoting and inhibiting formulations that comprise active agents conjugated to biodegradable sustained release polymers or water-insoluble biocompatible polymers may be selectively impregnated in porous surfaces on the implant. Alternatively, formulations comprising active agents conjugated to polymers may be used to selectively coat surfaces of the implant. In this sense, the polymer formulations may be considered coatings or cladding on the implant's surfaces.

In one particularly preferred embodiment, the tissue attachment promoting formulation comprises a series of time dependent growth factors in a time dependent release formulation. For example, depending on the type of surgery and type of implant utilized, various growth factors may be beneficial, including vascular growth promoting factors, collagen stimulation agents, and bone growth promoting agents, each of which may be released at different times. In a preferred embodiment, the tissue attachment promoting formulation includes vascular growth promoting agents, osteoconductive and/or osteoinductive agents, and collagen/cartilage stimulation agents, each capable of being released a different times. Such a formulation will provide the requisite tissue attachment treatment at the requisite time.

Methods of making such a tissue attachment promoting formulation include combining the agent with a sustained release polymer or biodegradable polymer having variable release rates. Alternatively, each agent may be combined with a different polymer or other material capable of differential release of the agent. It is preferred that the vascular growth promoting agents or factors be released first, so it is preferred that these agents be combined or otherwise coupled or conjugated to a polymer capable of relatively quick release. Preferably, the collagen/cartilage stimulation agents are released after the vascular growth promoting agents or factors, and finally, the osteoconductive and/or osteoinductive agents can be release last. These osteoconductive and/or osteoinductive agents therefore can be combined or otherwise coupled or conjugated to a polymer capable of slower release than those utilized for the vascular growth promoting agents. Using the guidelines provided herein, and coupled with the knowledge of delayed or sustained release formulation technology, those skilled in the art will be capable of designing a suitable time dependent release tissue attachment promotion formulation in accordance with the preferred embodiments.

Methods of treatment of the surfaces of medical implants with tissue attachment promoting and inhibiting formulations that have been described herein include providing a selectively porous implant surface, selectively impregnating porous implant surfaces with the appropriate formulations, selectively coating implant surfaces with the appropriate formulations, and selectively attaching or applying cladding with the appropriate formulations to implant surfaces. It should be understood that embodiments are not limited to a specific method of applying the tissue attachment promoting and inhibiting formulations, but rather encompass all such applicable methods of apply the formulations. One of skill in the art will recognize still other methods, and all such methods are contemplated for use herein.

The foregoing detailed description is provided to describe the invention in detail, and is not intended to limit the invention. Those skilled in the art will appreciate that various modifications may be made to the invention without departing significantly from the spirit and scope thereof.

What is claimed is:

1. A method for promoting selective endogenous tissue attachment to an osteoimplant, comprising:
   providing an osteoimplant having at least one endogenous tissue contacting surface where endogenous tissue attachment is desired, and at least one endogeneous tissue contacting surface where endogenous tissue attachment is not desired;

treating surfaces of the osteoimplant where endogenous tissue attachment is desired with a tissue attachment promoting treatment; and treating surfaces of the osteoimplant where endogenous tissue attachment is not desired with an endogenous tissue attachment inhibiting treatment wherein the tissue attachment promoting treatment comprises a tissue attachment formulation comprising a series of growth factors in a time dependent release formulation, the formulation comprising at least two agents selected from the group consisting of vascular growth promoting agents or factors, collagen/cartilage stimulation agents, osteoconductive agents and/or osteoinductive agents, and mixtures thereof, the at least two agents being combined with a sustained release polymer or biodegradable polymer having variable release rates such that at least one agent is released prior to an at least second agent.

2. The method of claim 1, wherein the tissue attachment promoting treatment comprises administration of at least a vascular growth promoting formulation and a bone attachment promoting formulation to at least the implant surfaces where bone attachment is desired.

3. The method of claim 2, wherein the tissue attachment promoting formulation is applied by a process selected from the group consisting of soaking, dip-coating, spray-coating, solution coating, powder coating, and combinations thereof.

4. The method of claim 2, wherein the tissue attachment promoting formulation comprises at least one component selected from the group consisting of: Bone Morphogenetic Proteins (BMPs), Osteoprotegerin, Connective Tissue Growth Factors (CTGFs), Vascular Endothelial Growth Factors (VEGFs), Transforming Growth Factor-betas (TGF-bs), Growth Differentiation Factors (GDFs), Cartilage Derived Morphogenic Proteins (CDMPs), Lim Mineralization Proteins (LMPs), hydroxyapatite (HA), tricalcium phosphate (TCP), collagen, fibronectin (FN), osteonectin (ON), endothelial cell growth factor (ECGF), cementum attachment extracts (CAE), ketanserin, human growth hormone (HGH), animal growth hormones, epidermal growth factor (EGF), human alpha thrombin, insulin-like growth factor (IGF), platelet derived growth factors (PDGF), fibroblast growth factors (FGF), and mixtures and combinations thereof.

5. The method of claim 1, wherein the endogenous tissue attachment inhibiting treatment comprises administration of a tissue attachment inhibiting formulation to at least the implant surfaces where endogenous tissue attachment is not desired.

6. The method of claim 5, wherein the tissue attachment inhibiting formulation comprises a component selected from the group consisting of chemotherapeutics, anti-adhesion agents, and mixtures and combinations thereof 7. The method of claim 5, wherein the tissue attachment inhibiting formulation is applied by a process selected from the group consisting of soaking, dip-coating, spray-coating, solution coating, powder coating, and combinations thereof.

8. The method of claim 1, wherein the endogenous tissue attachment inhibiting treatment comprises a physical transformation of at least the implant surfaces where endogenous tissue attachment is not desired.

9. The method of claim 8, wherein the physical transformation comprises the use of a process selected from the group consisting of: polishing, buffing, polycrystalline diamond deposition, the application of smooth cladding, the application of bio-inert materials, the application of bio-resorbable materials, and combinations thereof.

10. An osteoimplant comprising at least one endogenous tissue contacting surface, and at least one secondary endogenous tissue contacting surface where endogenous tissue attachment is not desirable, where the at least one endogenous tissue contacting surface comprises a tissue attachment promoting treatment, and the at least one secondary surface comprises an endogenous tissue attachment inhibiting treatment; wherein the tissue attachment promoting treatment comprises a tissue attachment formulation comprising a series of growth factors in a time dependent release formulation, the formulation comprising at least two agents selected from the group consisting of vascular growth promoting agents or factors, collagen/cartilage stimulation agents, osteoconductive agents and/or osteoinductive agents, and mixtures thereof, the at least two agents being combined with a sustained release polymer or biodegradable polymer having variable release rates such that at least one agent is released prior to an at least second agent.

11. The osteoimplant of claim 10, wherein the tissue attachment promoting treatment comprises at least a vascular growth promoting formulation and a bone attachment promoting formulation on bone contacting surfaces of the implant.

12. The osteoimplant of claim 11, wherein the tissue attachment promoting formulation comprises a component selected from the group consisting of: Bone Morphogenetic Proteins (BMPs), Osteoprotegerin, Connective Tissue Growth Factors (CTGFs), Vascular Endothelial Growth Factors (VEGFs), Transforming Growth Factor-betas (TGF-bs), Growth Differentiation Factors (GDFs), Cartilage Derived Morphogenic Proteins (CDMPs), Lim Mineralization Proteins (LMPs), hydroxyapatite (HA), tricalcium phosphate (TCP), collagen, fibronectin (FN), osteonectin (ON), endothelial cell growth factor (ECGF), cementum attachment extracts (CAE), ketanserin, human growth hormone (HGH), animal growth hormones, epidermal growth factor (EGF), human alpha thrombin, insulin-like growth factor (IGF), platelet derived growth factors (PDGF), fibroblast growth factors (FGF), and mixtures and combinations thereof.

13. The osteoimplant of claim 10, wherein the endogenous tissue attachment inhibiting treatment comprises a tissue attachment inhibiting formulation on at least one secondary surface.

14. The osteoimplant of claim 13, wherein the tissue attachment inhibiting formulation comprises a component selected from the group consisting of chemotherapeutics, anti-adhesion agents, and mixtures and combinations thereof 15. The osteoimplant of claim 10, wherein the endogenous tissue attachment inhibiting treatment comprises a physically transformed secondary surface.

16. The osteoimplant of claim 15, wherein the physically transformed secondary surface comprises a surface transformed by a process selected from the group consisting of: polishing, buffing, polycrystalline diamond deposition, the application of smooth cladding, the application of bio-inert materials, the application of bio-resorbable materials, and combinations thereof 17. The method of claim 1, wherein the tissue attachment formulation comprises vascular growth promoting agents or factors, collagen/cartilage stimulation agents, and osteoconductive and/or osteoinductive agents, each combined with a different sustained release polymer or biodegradable polymer having variable release rates.

18. The method of claim 17, wherein the tissue attachment formulation is configured to release the vascular growth promoting agents or factors first, the collagen/cartilage stimulation agents after the vascular growth promoting agents or factors, and the osteoconductive and/or osteoinductive agents last.

19. The osteoimplant of claim 10, wherein the tissue attachment formulation comprises vascular growth promoting agents or factors, collagen/cartilage stimulation agents, and osteoconductive and/or osteoinductive agents, each combined with a different sustained release polymer or biodegradable polymer having variable release rates.

20. The osteoimplant of claim 19, wherein the tissue attachment formulation is configured to release the vascular growth promoting agents or factors first, the collagen/cartilage stimulation agents after the vascular growth promoting agents or factors, and the osteoconductive and/or osteoinductive agents last.

\* \* \* \* \*